(12) United States Patent
Shi

(10) Patent No.: US 6,365,619 B1
(45) Date of Patent: Apr. 2, 2002

(54) TREATMENT OF ARTERIOSCLEROSIS

(75) Inventor: Victor Chengwei Shi, Short Hills, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/358,526

(22) Filed: Jul. 22, 1999

(51) Int. Cl.[7] ..................... A61K 31/405; A61K 31/215
(52) U.S. Cl. ........................ 514/415; 514/507
(58) Field of Search ................. 514/428, 415, 514/507

(56) References Cited

U.S. PATENT DOCUMENTS 5,675,062 A   10/1997   Haber et al. ................... 800/2

FOREIGN PATENT DOCUMENTS

WO   WO 96/03430   2/1996

OTHER PUBLICATIONS

U.S. Ser. No. 09/233,517, filed Jan. 19, 1999.

Primary Examiner—Theodore J. Criares
(74) Attorney, Agent, or Firm—Gabriel Lopez

(57) ABSTRACT

A method is disclosed of treating transplant-associated arteriosclerosis in a mammal which comprises administering to a mammal, preferably man, in need of such treatment an effective amount of a VLA-4 antagonist of formula I and a VCAM-1 inhibitor of formula II.

7 Claims, No Drawings

TREATMENT OF ARTERIOSCLEROSIS

BACKGROUND OF THE INVENTION

Transplant-associated arteriosclerosis (a manifestation of chronic rejection), defined as the formation of concentric intimal thickening in blood vessels of a transplanted solid organ, remains a paramount obstacle to long term graft survival; despite the availability of current immunosuppressive therapies. Although the pathogenesis of this disease remains unclear, both clinical and laboratory studies indicate that the arteriosclerosis associated with transplantation of solid organs is a complex, multi-factorial, immune-mediated process in which both donor vessel wall cells and recipient mononuclear cells play a pivotal role.

Adhesion molecules are involved in the early events of chronic rejection including leukocyte attachment and transendothelial cell migration. Cell adhesion (i.e., a process by which cells associate with each other, migrate towards a specific target, or localize within the extracellular matrix) underlies many biological phenomena. Cell adhesion causes adhesion of hemoatopoietic to endothelial cells and the subsequent migration of those hemopoietic cells out of blood vessels and to the site of injury, thus playing a role in mammalian pathologies such as inflammation and immune reactions.

Various cell-surface macromolecules (known as cell adhesion receptors) mediate cell—cell and cell-matrix interactions. For example, the integrins are the key mediators in adhesive interactions between hematopoietic and other cells. Integrins are non-covalent heterodimeric complexes consisting of two subunits, $\alpha$ and $\beta$. Depending on the type of its $\alpha$ and $\beta$ subunit components, each integrin molecule is categorized into its own subfamily. There are at least 12 different $\alpha$ subunits ($\alpha 1$–$\alpha 6$, $\alpha$-L, $\alpha$-M, $\alpha$-X, $\alpha$-IIB, $\alpha$-V, and $\alpha$-E) and at least 9 different $\beta$ subunits ($\beta 1$–$\beta 9$).

The very late antigen-4 (VLA-4), also known as $\alpha 4\beta 1$ integrin or CD49d/CD29, is a leukocyte cell surface receptor that participates in a variety of cell-cell and cell-matrix adhesions. It is a receptor for both the cytokine-inducible endothelial cell surface protein, the extracellular matrix protein fibronectin (FN), and the vascular cell adhesion molecule-1 (VCAM-1), which is an immunoglobulin superfamily member mainly expressed on activated endothelium and antigen presenting cells. Anti-VLA-4 monoclonal antibodies (mAb's) inhibit VLA-4-dependent adhesive interactions both in vitro and in vivo.

Cellular adhesion molecules such as selectins, integrins, and the VCAM-1 immunoglobulin superfamily are considered to be central in T cell activation, recognition of alloantigens, leukocyte rolling, attachment, and transendothelial migration. The earliest histopathological change following allo-transplantation is increased mononuclear inflammatory cell adhesion to the vascular endothelium.

VCAM-1/VLA-4 interactions alone, or in combination with another pair of molecules (LFA-1 on T cells and ICAM-1 on activated endothelial cells) mediate lymphocyte adhesion and transmigration at the vascular endothelial surface, and possibly provide the stimulus for the development of accelerated arteriosclerosis. Upon transmigration, activated lymphocytes release cytokines, growth factors, and chemotactic agents within the vessel wall to stimulate proliferation and migration of smooth muscle cell (SMC) into the developing neointima.

The role of VCAM-1 and VLA-4 expression in chronic rejection is not well understood in part due to the lack of genetically manipulated mice (knock out of either alpha-4 integrin or VCAM-1 is lethal).

SUMMARY OF THE INVENTION

It has now been found that the concomitant administration of a VLA-4 antagonist of formula I and a VCAM-1 inhibitor of formula II is useful in treating transplant-associated arteriosclerosis.

DETAILED DESCRIPTION

Accordingly, the present invention utilizes compounds of formula I

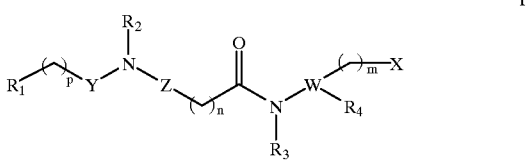

wherein $R_1$ is alkyl, alkenyl, alkynyl, cycloalkyl, aryl-fused cycloalkyl, cycloalkenyl, aryl, aryl-substituted alkyl (aralkyl), aryl-substituted alkenyl or alkynyl, cycloalkyl-substituted alkyl, cycloalkenyl-substituted cycloalkyl, biaryl, alkoxy, alkenoxy, alkynoxy, aryl-substituted alkoxy (aralkoxy), aryl-substituted alkenoxy or alkynoxy, alkylamino, alkenylamino or alkynylamino, aryl-substituted alkylamino, aryl-substituted alkenylamino or alkynylamino, aryloxy, arylamino, N-alkylureido-substituted alkyl, N-arylureido-substituted alkyl, alkylcarbonylamino-substituted alkyl, aminocarbonyl-substituted alkyl, heterocyclyl, heterocyclyl-substituted alkyl, heterocyclyl-substituted amino, carboxyalkyl substituted aralkyl, oxocarbocyclyl-fused aryl, or heterocyclylalkyl;

$R_2$ is $(CH_2)_q$—V—$(CH_2)_{q'}$—$V_r$—$R_8$;

$R_3$ is H, alkyl, alkenyl, aryl, or heteroaryl;

$R_4$ is H, aryl, alkyl, cycloalkyl, alkenyl, cycloalkenyl, alkynyl and aryl-substituted alkyl, heterocyclyl, heterocyclylcarbonyl, aminocarbonyl, amido, mono- or dialkylaminocarbonyl, mono- or diarylaminocarbonyl, alkylarylaminocarbonyl, diarylaminocarbonyl, mono- or diacylaminocarbonyl, aromatic or aliphatic acyl, or alkyl optionally substituted by substituents selected from the group consisting of amino, halo, hydroxy, mercapto, mono- or dialkylamino, mono- or diarylamino, alkylarylamino, mono- or diacylamino, alkoxy, alkenoxy, aryloxy, thioalkoxy, thioalkenoxy, thioalkynoxy, thioaryloxy, and heterocyclyl;

$R_5$ is alkyl, alkenyl, alkynyl, cycloalkyl, cycloalkenyl, aryl, aryl-substituted alkyl, aryl-substituted alkenyl, or alkynyl; alkyl optionally substituted by substituents selected from the group consisting of amino, halo, hydroxy, mercapto, mono- or dialkylamino, mono- or diarylamino, alkylarylamino, mono- or diacylamino, alkoxy, alkenoxy, aryloxy, thioalkoxy, thioalkenoxy, thioalkynoxy, thioaryloxy, and heterocyclyl;

$R_6$ is alkyl, alkenyl, alkynyl, cycloalkyl, cycloalkenyl, aralkyl, aryl-substituted alkenyl or alkynyl, hydroxy-substituted alkyl, alkoxy-substituted alkyl, aralkoxy-substituted alkyl, amino-substituted alkyl, (aryl-substituted alkyloxycarbonylamino)-substituted alkyl, thiol-substituted alkyl, alkylsulfonyl-substituted alkyl, (hydroxy-substituted alkylthio)-substituted alkyl, thioalkoxy-substituted alkyl, acylamino-substituted alkyl, alkylsulfonylamino-substituted alkyl, arylsulfonylamino-substituted alkyl, morpholino-alkyl, thiomorpholino-alkyl, morpholinocarbonyl-substituted alkyl, thiomorpholinocarbonyl-substituted alkyl, [N-(alkyl, alkenyl or alkynyl)- or (N,N-dialkyl, dialkenyl or dialkynyl)-amino] carbonyl-substituted alkyl, carboxyl-substituted alkyl, dialkylamino-substituted acylaminoalkyl; or amino acid side chains selected from arginine, asparagine, glutamine, S-methyl cysteine, methionine and corresponding sulfoxide and sulfone derivatives thereof, glycine, leucine, isoleucine, allo-isoleucine, tert-leucine, norleucine, phenylalanine, tyrosine, tryptophan, proline, alanine, ornithine, histidine, glutamine, valine, threonine, serine, aspartic acid, beta-cyanoalanine, and allothreonine;

$R_7$ and $R_8$ are independently H, alkyl, alkenyl, carbocyclic aryl, heteroaryl, or alkyl, alkenyl, carbocyclic aryl or heteroaryl substituted by 1–3 substituents selected from the group consisting of amino, hydroxy, mercapto, mono- or dialkylamino, mono- or diarylamino, alkylarylamino, diarylamino, mono- or diacylamino, alkoxy, alkenoxy, aryloxy, thioalkoxy, thioalkenoxy, thioalkynoxy, thioaryloxy, and heterocyclyl;

or $R_2$ and $R_6$ taken together with the atoms to which they are attached may form a heterocycle;

V is O, NH, S, SO, or $SO_2$;

X is $CO_2R_5$, $PO_3H$, $SO_2R_5$, $SO_3H$, $OPO_3H$, $CO_2H$, or $CON(R_4)_2$;

W is CH or N;

Y is CO, $SO_2$, or $PO_2$;

Z is $(CH_2)_n$, $CHR_6$, or $NR_7$;

n and n' are independently 0–4;

m is 1–4;

p is 1–4;

q and q' are independently 1–5; and r is 0 or 1;

or pharmaceutically acceptable salts thereof.

The present invention also utilizes compounds of the formula II

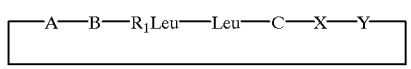

wherein:

A is an α-hydroxy-substituted butyric acid residue optionally γ-substituted by $R_6$, which is CN, —$COOR_2$, —$CONR_3R_4$, —$COR_5$, —$CSNH_2$ or alkyl, which may be substituted by azido, halogen, alkoxy, optionally protected hydroxy or amino, vinyl, which may be substituted by alkyl, halogen or CN, cycloalkyl, tetrazolyl or —C≡CH, wherein $R_2$ is hydrogen or optionally arylsubstituted alkyl, $R_3$ and $R_4$ are the same or different and represent hydrogen or alkyl or form together with the nitrogen a 3- to 6-membered ring optionally containing a second heteroatom, and $R_5$ is hydrogen or lower alkyl;

B is an α-amino-γ-methyl-substituted octanoic acid residue;

$R_1$ is hydrogen or methyl;

C is a tryptophan or N-methyl-tryptophan residue of formula VI

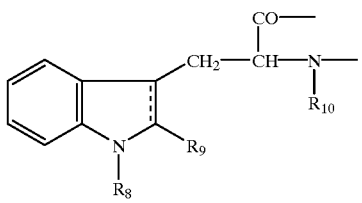

wherein $R_8$ is hydrogen, alkoxy, alkyl or benzyl;

$R_9$ is hydrogen or halogen;

$R_{10}$ is hydrogen or methyl;

X is an α-amino-substituted ($C_2$ to $C_{14}$) carboxylic acid residue;

Y is an α-amino- or N-methyl-α-amino substituted ($C_2$–$C_{10}$) carboxylic acid residue; and

- - - is a single or double bond.

In formula II the C-terminal to N-terminal, orientation of the amino acid residues is in the clockwise direction, and the peptolide ester bond is between residues A and Y. When $R_1$ is methyl, the residues $R_1$-Leu and Leu are N-methyl-leucine and leucine residues, respectively.

Preferably, A is an α-hydroxybutyric acid residue, which is γ-substituted by cyano, —$COOR_2'$, wherein $R_2'$ is hydrogen, lower alkyl with 1 to 4 carbon atoms or diphenylmethyl, —$CONR_3'R_4'$, wherein $R_3'$ is hydrogen or methyl, and $R_4'$ is hydrogen or alkyl or $R_3'$ and $R_4'$ form together with the nitrogen a 3- to 6-membered ring or a morpholinyl ring, —$CH_2OH$, —$COR_5'$, wherein $R_5'$ is hydrogen or lower alkyl with 1 to 4 carbon atoms, vinyl optionally substituted by CN, Br or lower alkyl with 1 to 4 carbon atoms, alkyl optionally substituted by azido, amino, hydroxy, chloro or alkoxy, tetrazolyl, cyclopropyl, —$CSNH_2$ or —C≡CH.

Preferably, C is a N-methyltryptophan residue of formula VI, wherein $R_8$ is hydrogen, ($C_1$ to $C_4$)alkoxy, especially methoxy, or alkyl and $R_9$ is hydrogen or halogen.

Preferably, X is an α-amino-substituted ($C_4$ to $C_8$) carboxylic acid residue, which is optionally β- or γ-($C_1$ to $C_4$) alkyl substituted. Most preferably, X is an α-amino-β- or γ-($C_1$ to $C_4$)alkyl-, especially methyl-, substituted octanoic or a butyric acid residue.

Preferably, Y is an N-methyl-α-amino-substituted ($C_2$ to $C_4$) carboxylic acid residue, which is optionally β- or γ-($C_1$ to $C_4$) alkyl-substituted. Most preferably, Y is an N-methyl-alanine or N-methyl-valine residue.

The compounds of formula II comprise asymmetric C-atoms and these may be in either the R or S configuration.

The invention includes open chain peptides or peptolides corresponding to the compounds of formula II; for instance, the open chain molecules obtained by either cleavage of the ester bond between residues Y and A or cleavage of an amide linkage between any other adjacent pair of the acid residues. Preferred open-chain derivatives are compounds of formulae IV and V

    IV

    V wherein $R_1$ is hydrogen or methyl and $R_7$ is hydrogen or alkyl.

A preferred subgroup of compounds is the compounds of formula IIp

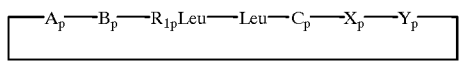

$II_p$ wherein:
- $A_p$ is an α-hydroxy-substituted butyric acid residue optionally γ-substituted by $R_{6p}$, which is CN, optionally protected —$CH_2OH$, —$COOR_{2p}$, —$CONR_{3p}R_{4p}$, —$COR_{5p}$ or —$CH=CH_2$, wherein $R_{2p}$ is hydrogen or optionally arylsubstituted alkyl, $R_{3p}$ and $R_{4p}$ are the same or different and represent hydrogen or alkyl or form together with the nitrogen a 5- or 6-membered ring optionally containing a second heteroatom, and $R_{5p}$ is hydrogen or lower alkyl;
- $B_p$ is an α-amino-γ-methyl-substituted octanoic acid residue;
- $R_{1p}$ is hydrogen or methyl;
- $C_p$ is a tryptophan or N-methyl-tryptophan residue, which is optionally N'-($C_1$ to $C_4$) alkoxy substituted;
- $X_p$ is an α-amino-substituted ($C_2$ to $C_{14}$) carboxylic acid residue; and
- $Y_p$ is an α-amino- or N-methyl-γ-amino substituted ($C_2$ to $C_{10}$) carboxylic acid residue.

A further subgroup of the compounds of the invention are the compounds of formula II'p

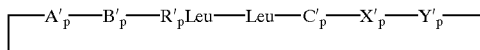

$II'_p$ wherein:
- $A'_p$ is an α-hydroxy-substituted butyric acid residue optionally γ-substituted by $R'_{6p}$, which is CN, —$COOR'_{2p}$, —$CONR'_{3p}R'_{4p}$, —$COR'_{5p}$, alkyl, which may be substituted by azido, halogen, alkoxy, optionally protected hydroxy or amino, vinyl, which may be substituted by alkyl, halogen or CN, cycloalkyl, tetrazolyl or —C≡CH, wherein $R'_{2p}$ is hydrogen or optionally arylsubstituted alkyl, $R'_{3p}$ and $R'_{4p}$ are the same or different and are hydrogen or alkyl or form together with the nitrogen a 3- to 6-membered ring optionally containing a second heteroatom, and $R'_{5p}$ is hydrogen or lower alkyl;
- $B'_p$ is an α-amino-γ-methyl-substituted octanoic acid residue;
- $R'_{1p}$ is hydrogen or methyl; and
- $C'_p$ is a tryptophan or N-methyl-tryptophan residue of formula VIp'

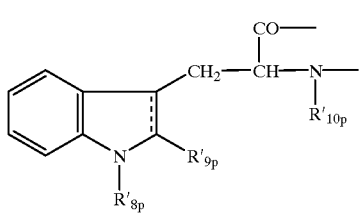

$VI'_p$ wherein
- $R'_{8p}$ is hydrogen, alkoxy, alkyl or benzyl;
- $R'_{9p}$ is hydrogen or halogen;
- $R'_{10p}$ is hydrogen or methyl;
- $X'_p$ is an α-amino-substituted ($C_2$–$C_{14}$) carboxylic acid residue;
- $Y'_p$ is an α-amino- or N-methyl-α-amino substituted ($C_2$–$C_{10}$) carboxylic acid residue; and
- - - - is a single or double bond.

Also, the invention includes use of all the compounds of the invention when in salt or ester form as well as in free form.

A particularly preferred compound of formula II is a compound of formula II'

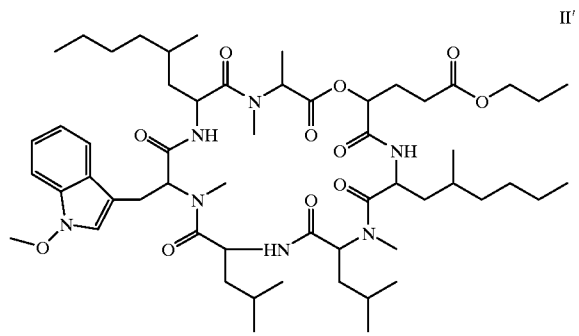

II'

This compound is referred to herein as compound 741. It is Example 15 of PCT application WO 96/03430.

The compounds of formula II are described in PCT application WO 96/03430 (Feb. 8, 1996) and in co-pending U.S. patent application Ser. No. 08/776,440 (Jan. 24, 1997), both of which are incorporated herein by reference.

An embodiment of the invention is a pharmaceutical composition comprising effective amounts of the compounds of formula I and formula II, optionally further comprising one or more pharmaceutically acceptable carriers.

The invention provides the concomitant administration of effective amounts of the compounds of the invention, i.e., compounds of formula I and formula II, to a mammal, preferably man, in need of treatment, preferably the treatment of transplant-associated arteriosclerosis.

In a further aspect the invention provides a method of treating transplant-associated arteriosclerosis in a mammal which comprises administering to a mammal, preferably man, in need of such treatment an effective amount of the compounds of the invention. Transplantation may be xeno- or allotransplantaion (e.g., porcine-human or human—human).

Particular embodiments of the invention relate to compounds of formula I or pharmaceutically acceptable salts thereof wherein (a) $R_1$ is aryl, particularly N-arylureido-substituted phenyl;
(b) $R_4$ is H, alkyl, alkenyl or aryl;
(c) W is CH;
(d) Y is CO;
(e) X is $CO_2H$ or $CO_2$alkyl; and
(f) Z is $(CH_2)_{n'}$ or $CHR_6$.

Preferred compounds of the invention are those of formula Ia

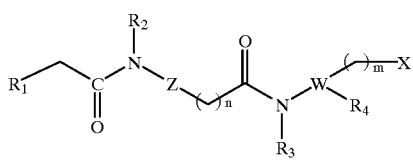

Ia wherein $R_2$ is $C_{1-4}$alkyl-oxy-$C_{1-8}$alkyl;

$R_4$ is H, alkyl, alkenyl, carbocyclic aryl or heteroaryl;

X is $CO_2H$ or $CO_2$alkyl;

and the other symbols are as defined for formula I; or pharmaceutically acceptable salts thereof.

More-preferred compounds of the invention are those of formula Ia wherein $R_1$ is aryl; $R_2$ is methoxy-n-propyl; $R_3$ is H; $R_4$ is alkenyl or aryl; X is $CO_2H$; n is 0; and W is CH; or pharmaceutically acceptable salts thereof.

A particular embodiment of the invention is directed to compounds of formula Ib

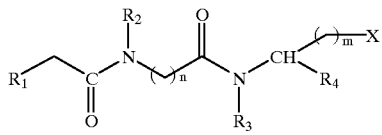

Ib wherein $R_1$ is N-arylureidophenyl;

$R_2$ is $C_1$–$C_4$-alkyl-oxy-$C_2$–$C_4$-alkyl;

$R_3$ is H;

$R_4$ is H, $C_1$–$C_4$-alkyl, $C_2$–$C_4$-alkenyl or carbocyclic aryl;

n is 1 or 2;

m is 1, 2 or 3;

X is COOH or $CO_2R_5$; and $R_5$ is optionally substituted lower alkyl;

or pharmaceutically acceptable salts thereof.

Preferred are the compounds of formula Ib wherein $R_1$ is N-(optionally substituted phenyl)-ureidophenyl;

$R_2$ is methoxypropyl;

$R_3$ is H;

$R_4$ is $C_2$–$C_4$-alkenyl or optionally substituted phenyl;

n is 1;

m is 1; and

X is COOH;

or pharmaceutically acceptable salts thereof.

Another particular embodiment of the invention is directed to compounds of formula Ic

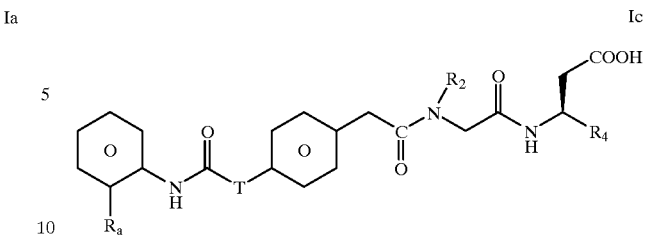

Ic wherein $R_a$ is H, $CH_3$, Cl or $NH_2$;

$R_2$ is $(CH_2)_3OCH_3$ or $(CH_2)_4OCH_3$;

$R_4$ is —(CH)=(CH)—$CH_3$, phenyl, 4-methoxyphenyl, or 3,4-dimethoxyphenyl; and T is NH or $CH_2$;

or pharmaceutically acceptable salts thereof.

Most-preferred compounds of the invention are those of formula Id

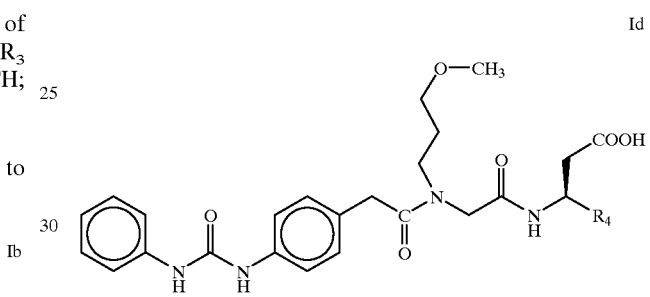

Id wherein $R_4$ is —(CH)=(CH)—$CH_3$, phenyl, 4-methoxyphenyl, or 3,4-dimethoxyphenyl;

or the pharmaceutically acceptable salts thereof. Of these the preferred compound is that wherein $R_4$ is 3,4-dimethoxyphenyl, which is referred to herein as compound 369.

"Alkyl" means a straight-chain or branched-chain alkyl radical containing from 1 to 10, preferably from 1 to 6, and more preferably from 1 to 4, carbon atoms. Examples of such radicals include methyl, ethyl, n-propyl, isopropyl, n-butyl, isobutyl, sec-butyl, tert-butyl, pentyl, iso-amyl, hexyl, and decyl.

"Alkenyl" means a straight-chain or branched-chain alkenyl radical containing from 2 to 10, preferably from 2 to 6, and more preferably from 2 to 4, carbon atoms. Examples of such radicals include etheryl, E- and Z-propenyl, isopropenyl, E- and Z-butenyl, E- and Z-isobutenyl, E- and Z-pentenyl, and decenyl.

"Lower" in conjunction with the above terms means a said radical containing up to 6 carbon atoms.

"Substituted" in conjunction with the above terms means a said radical substituted by e.g. amino, halo, hydroxy, mercapto, mono- or dialkylamino, mono- or di-arylalkylamino, mono- or diarylamino, alkoxy, aryloxy, aryl, thioaryloxy, thioalkoxy or heterocyclyl.

"Alkynyl" means a straight-chain or branched-chain alkynyl radical containing from 2 to 10, preferably from 2 to 6, and more preferably from 2 to 4, carbon atoms. Examples of such radicals include ethynyl (acetylenyl), propynyl, propargyl, butynyl, hexynyl, and decynyl.

"Cycloalkyl" means a cyclic alkyl radical containing from 3 to 8, preferably from 3 to 6, carbon atoms. Examples of such cycloalkyl radicals include, cyclopropyl, cyclobutyl, cyclopentyl, cyclohexyl, and cyclopropyl methyl.

"Cycloalkenyl" means a cyclic carbocycle containing from 4 to 8, preferably 5 to 6, carbon atoms and one or more double bonds. Examples of such cycloalkenyl radicals include cyclopentenyl, cyclohexenyl, cyclopentadienyl, and 2-methyl-2-butenyl.

Aryl means carbocyclic or heterocyclic aryl (heteroaryl).

"Aryl" (carbocyclic aryl and heteroaryl) means a 5- or 6-membered carbocyclic aromatic or heteroaromatic ring containing 0–3 heteroatoms selected from O, N, and S; a bicyclic 9- or 10-membered aromatic or heteroaromatic ring system containing 0–3 heteroatoms selected from O, N, and S; or a tricyclic 13- or 14-membered aromatic or heteroaromatic ring system containing 0–3 heteroatoms selected from O, N, and S; each of which rings is optionally substituted with 1–3 substituents selected from e.g. lower alkyl, alkenyl, alkynyl, substituted lower alkyl, substituted alkenyl, substituted alkynyl, =O, $NO_2$, halogen, hydroxy, alkoxy, cyano, —NR'R', acylamino, phenyl, benzyl, phenoxy, benzyloxy, heteroaryl, and heteroaryloxy, wherein each of said phenyl, benzyl, phenoxy, benzyloxy, heteroaryl, and heteroaryloxy is optionally substituted with 1–3 substituents selected from e.g. lower alkyl, alkenyl, alkynyl, halogen, hydroxy, alkoxy, cyano, phenyl, phenoxy, benzyl, benzyloxy, carboxy, carboalkoxy, carboxamido, heteroaryl, heteroaryloxy, $NO_2$, and —NR' R', wherein R' is H or lower alkyl. The carbocyclic aromatic ring systems comprise phenyl, naphthyl, indenyl, indanyl, azulenyl, fluorenyl, anthracenyl. The heterocyclic aromatic ring systems comprise furyl, thienyl, pyridyl, pyrrolyl, oxazolyly, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl.

"Aryl", as it relates in particular to the grouping $R_1$ in the above formulae, means carbocyclic or heterocyclic aryl, particularly phenyl optionally substituted by one to three substituents which are independently selected from e.g. halo, hydroxyl, amino, nitro, trifluoromethyl, trifluoromethoxy, alkyl, alkenyl, alkynyl, cyano, carboxy, carboalkoxy, Ar'-substituted alkyl, Ar'-substituted alkenyl or alkynyl, 1,2-dioxymethylene, 1,2-dioxyethylene, alkoxy, alkenoxy or alkynoxy, Ar'-substituted alkoxy, Ar'-substituted alkenoxy or alkynoxy, alkylamino, alkenylamino or alkynylamino, Ar'-substituted alkylamino, Ar'-substituted alkenylamino or alkynylamino, Ar'-substituted carbonyloxy, alkylcarbonyloxy, aliphatic or aromatic acyl such as alkanoyl, Ar'-substituted alkanoyl or Ar'-substituted carbonyl, Ar'-substituted alkylcarbonyloxy, Ar'-substituted carbonylamino, Ar'-substituted amino, Ar'-substituted oxy, alkylcarbonylamino, Ar'-substituted alkylcarbonylamino, Ar'-substituted aminocarbonylalkyl, alkoxy-carbonylamino, Ar'-substituted alkoxycarbonyl-amino, Ar'-oxycarbonylamino, alkylsulfonylamino, mono- or bis- (Ar'-sulfonyl) amino, Ar'-substituted alkyl-sulfonylamino, morpholinocarbonylamino, thiomorpholinocarbonylamino, N-alkyl guanidino, N-Ar' guanidino, N-Ar' cyano-guanidino, N-N- (Ar'-, alkyl) guanidino, N,N- (Ar', Ar') guanidino, N,N-dialkyl guanidino, N,N,N-trialkyl guanidino, N-alkyl-ureido, N,N-dialkyl-ureido, N-Ar'-ureido, N,N- (Ar',alkyl) ureido and N,N- (Ar')$_2$ ureido; acylcarbonylamino; Ar'-substituted aryl; aromatic acyl-substituted aromatic or aliphatic acyl; Ar'-substituted heterocyclyl;' Ar'-substituted cycloalkyl or cycloalkenyl; heterocyclylalkoxy; N,N-(Ar', hydroxyl) ureido; Ar'-substituted cycloalkyl and cycloalkenyl; Ar'-substituted biaryl; Ar'-substituted aminocarbonylamino; Ar'-mercapto-substituted alkyl; Ar'-amino-substituted aryl; Ar'-oxy-substituted alkyl; Ar'-substituted aminocycloalkyl and cycloalkenyl; aralkylaminosulfonyl; aralkoxyalkyl; N-Ar'-substituted thioureido; N-aralkoxyureido; N-hydroxylureido; N-alkenylureido; N,N-(alkyl, hydroxyl)ureido; heterocyclyl; thioaryloxy-substituted aryl; N,N-(aryl,alkyl)hydrazino; Ar'-substituted sulfonylheterocyclyl; aralkyl-substituted heterocyclyl; cycloalkyl and cycloalkenyl-substituted heterocyclyl; cycloalkyl-fused aryl; aryloxy-substituted alkyl; heterocyclylamino; Ar'-substituted arylaminosulfonyl; Ar'-substituted alkenoyl; aliphatic or aromatic acylaminocarbonyl; aliphatic or aromatic acyl-substituted alkenyl; Ar'-substituted aminocarbonyloxy; Ar',Ar'-disubstituted aryl; aliphatic or aromatic acyl-substituted acyl; benzofused-heterocyclylcarbonylamino; Ar'-substituted hydrazino; Ar'-substituted aminosulfonyl; Ar'-substituted alkylamino; Ar'-substituted heterocyclyl; Ar',Ar'-disubstituted alkanoylamino; Ar'-substituted cycloalkanoylamino; heterocyclylalkoxy; N,N-Ar',hydroxylureido; N,N'-Ar', hydroxylureido; heterocyclylcarbonylamino; Ar'-substituted aminocarbonylheterocyclyl; Ar'-substituted aminocarbonyl; Ar'-substituted carbonylamino; Ar'-substituted aminosulfonylamino; Ar'-substituted mercaptoalkyl; Ar'-amino substituted biaryl; aralkylaminoalkoxy; alkyl- and aryloxy-substituted alkoxy; heterocyclylcarbonyl; Ar'-substituted sulfonylalkyl; Ar'-amino carbocyclyl; aralkylsulfonyl; aryl-substituted alkenyl; heterocyclylalkylamino; heterocyclylalkylaminocarbonyl; Ar'-substituted sulfonylaminoalkyl; Ar'-substituted cycloalkyl; thioaryloxyalkyl; thioaryloxymercapto; cycloalkylcarbonylalkyl; cycloalkyl-substituted amino; Ar'-substituted arylamino; aryloxycarbonylalkyl; phosphorodiamidyl acid or ester; aryloxydimethylsiloxy; 1,3-indandionylcarbonylalkyl; 1,3-indandionylcarbonyl; oxamidyl; heterocyclylalkylidenyl; formamidinyl; benzalizinyl; benzalhydrazino; arylsulfonylureido; benzilylamino; 4-(N-2-carboxyalkyl-1-(1,3-benzodioxol-5-yl)-amino-N-leucinylalkylamidylarylurea); Ar'-carbamoyloxy and alkyl- and aryloxy-substituted ureido; wherein "Ar" is a carbocyclic or heterocyclic aryl group as defined above having one to three substituents selected from the group consisting of hydrogen, halogen, hydroxyl, amino, nitro, trifluoromethyl, trifluoromethoxy, alkyl, alkenyl, alkynyl, 1,2-dioxymethylene, 1,2-dioxyethylene, alkoxy, alkenoxy, alkynoxy, alkylamino, alkenylamino or alkynylamino, alkylcarbonyloxy, aliphatic or aromatic acyl, alkylcarbonylamino, alkoxycarbonylamino, alkylsulfonylamino, N-alkyl or N,N-dialkylureido.

"Alkoxy" means an alkyl ether radical. Examples of alkyl ether radicals include methoxy, ethoxy, n-propoxy, iso-propoxy, n-butoxy, iso-butoxy, sec-butoxy, and tert-butoxy. "Alkenoxy" means a radical of formula alkenyl-O—, provided that the radical is not an enol ether. Examples of alkenoxy radicals include allyloxy and E- and Z-3-methyl-2-propenoxy. "Alkynyloxy" means a radical of formula alkynyl-O—, provided that the radical is not an ynol ether. Examples of alkynoxy radicals include propargyloxy and 2-butynyloxy. "Thioalkoxy" means a thioether radical of the formula alkyl-S—.

"Alkylamino" means a mono- or di-alkyl-substituted amino radical (i.e., a radical of formula alkyl-NH— or (alkyl)$_2$-N—). Examples of alkylamino radicals include methylamino, ethylamino, propylamino, isopropylamino, t-butylamino, and N,N-diethylamino.

"Alkenylamino" means a radical of formula alkenyl-NH— or (alkenyl)$_2$N—, provided that the radical is not an enamine. An example of an alkenylamino radical is the allylamino radical.

"Alkynylamino" means a radical of formula alkynyl-NH— or (alkynyl)$_2$N—, provided that the radical is not an ynamine. An example of an alkynylamino radical is the propargyl amino radical.

"Aryloxy" means a radical of formula aryl-O—. Examples of aryloxy radicals include phenoxy, naphthoxy, and pyridyloxy.

"Arylamino" means a radical of formula aryl-NH—. Examples of arylamino radicals include phenylamino (anilido), naphthylamino, 2-, 3- or 4-pyridylamino. "Biaryl" means a radical of formula aryl-aryl—.

"Thioaryl" means a radical of formula aryl-S—. An example of a thioaryl radical is the thiophenyl radical.

"Aryl-fused cycloalkyl" means a cycloalkyl radical which shares two adjacent atoms with an aryl radical. An example of an aryl-fused cycloalkyl radical is the benzofused cyclobutyl radical.

"Aliphatic acyl" means a radical of the formula alkyl-CO—, alkenyl-CO—, or alkynyl-CO— derived from a carboxylic acid. Examples of aliphatic acyl radicals include acetyl, propionyl, butyryl, valeryl, 4-methylvaleryl, acryloyl, crotyl, propiolyl, and methylpropiolyl. "Aromatic acyl" means a radical of the formula aryl-CO—. Examples of aromatic acyl radicals include benzoyl, 4-halobenzoyl, 4-carboxybenzoyl, naphthoyl, and pyridylcarbonyl. "Morpholinocarbonyl" and "thiomorpholinocarbonyl" mean an N-carbonylated morpholino and an N-carbonylated thiomorpholino radical, respectively. "Alkylcarbonylamino" means a radical of formula alkyl—CONH—. "Alkoxycarbonylamino" means a radical of formula alkyl-OCONH—. "Alkylsulfonylamino" means a radical of formula alkyl-SO$_2$NH—. "Arylsulfonylamino" means a radical of formula aryl-SO$_2$NH—. "N-alkylurea" or "N-alkylureido" means a radical of formula alkyl-NH-CO-NH—. "N-arylurea" or "N-arylureido" means a radical of formula aryl-NH—CO-NH—. "Halogen" or "halo" means fluoro, chloro, bromo, and iodo.

"Heterocycle", unless otherwise defined herein, means a stable 3–7 membered monocyclic heterocyclic ring or an 8–11 membered bicyclic heterocyclic ring which is saturated or unsaturated, and which may be optionally benzofused. Each heterocycle consists of one or more carbon atoms and from one to four heteroatoms selected from nitrogen, oxygen, and sulfur, any oxidized form of nitrogen and sulfur, and the quaternized form of any basic nitrogen. Any ring nitrogen may be optionally substituted with a substituent R$^4$, as defined herein for compounds of formula I. A heterocycle may be attached at any endocyclic carbon or heteroatom which results in the creation of a stable structure. Preferred heterocycles include 5–7 membered monocyclic heterocycles and 8–10 membered bicyclic heterocycles. Heterocycles may be optionally oxo-substituted at 1–3 ring positions and may optionally be independently substituted with 1–4 aryl substituents. Included are heteroaryl groups as defined herein and saturated heterocycles such as piperidine, morpholine, pyrrolidine, thiazolidine, piperazine and the like.

It is intended that the definitions of any substituent or symbol in a particular molecule be independent of its definitions elsewhere in the molecule. Thus, for example, —N(R$_4$)$_2$ represents —NH$_2$, —NHCH$_3$, —N(CH$_3$)$_2$ etc.

Some of the compounds described herein contain one or more asymmetric centers and may thus give rise to enantiomers, diastereomers, and other stereoisomeric forms which may be defined in terms of absolute stereochemistry as (R) or (S), or as (D) or (L) for amino acids. The present invention is meant to include all such possible diastereomers as well as their racemic and optically pure forms. Optically active (R) and (S), or (D) and (L), isomers may be prepared using chiral synthons or chiral reagents, or resolved using conventional techniques. When the compounds described herein contain olefinic double bonds or other centers of geometric asymmetry, and unless specified otherwise, it is intended to include both E and Z geometric isomers. Likewise, all tautomeric forms are intended to be included.

In a preferred group of compounds of the invention, where W in formula I is CH, the stereochemistry at this carbon atom is (S), i.e. the compounds are of formula

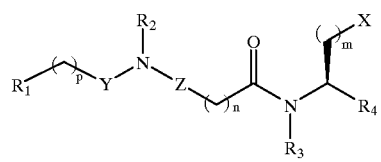

Ie where R$_1$, R$_2$, R$_3$, R$_4$, X, Y, Z, m, n and p are as defined for formula I, and their pharmaceutically acceptable salts.

The pharmaceutical compositions of the present invention comprise the compounds of formula I and formula II or pharmaceutically acceptable salts thereof as active ingredients, and may also contain one or more pharmaceutically acceptable carriers and, optionally, other therapeutic ingredients. The term "pharmaceutically acceptable salts" refers to salts prepared from pharmaceutically acceptable non-toxic acids or bases including organic and inorganic acids or bases.

When a compound of the present invention is acidic, salts may be prepared from pharmaceutically acceptable non-toxic bases. Salts derived from all stable forms of inorganic bases include aluminum, ammonium, calcium, copper, iron, lithium, magnesium, manganese, potassium, sodium, zinc, etc. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion-exchange resins such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucosamine, morpholine, piperazine, piperidine, polyamine resins, procaine, purine, theobromine, triethylamine, trimethylamine, tripropylamine, etc.

When a compound of the present invention is basic, salts may be prepared from pharmaceutically acceptable non-toxic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, mandelic, methanesulfonic, mucic, nitric, pamoic, pantothenic, phosphoric, succinic, sulfuric, tartaric, p-toluenesulfonic, etc. Particularly preferred are citric, hydrobromic, maleic, phosphoric, sulfuric, and tartaric acids. Base salts also include ammonium, alkali metal, and alkaline earth metal salts, salts with organic bases, such as dicyclohexylamine salts, and salts with amino acids such as arginine and lysine. Also, basic nitrogen-containing groups can be quaternized with such agents as lower alkyl halides, such as methyl chloride, dialkyl sulfates, such as dimethyl, sulfates, long chain halides such as stearyl chlorides, and aralkyl halides, such as benzyl chlorides.

By concomitant administration is meant administration of the compounds of formula I and II simultaneously or at approximately the same time (i.e., within 48 hours of each other, preferably within 24 hours, more preferably within 8 hours). Also, the mode of administration may be the same or different for each compound. Generally, there is no limitation on the sequence or mode of administration. Thus, the compounds may be administered in a single dosage form, either one can be administered first, one may be administered orally and the other intravenously, one may be administered continuously and the other intermittantly, etc Administration may begin shortly (e.g., 1–5 days) before transplantation or at the time thereof or as soon as possible thereafter to maximize the effect of treatment.

The magnitude of the prophylactic or therapeutic dose of the compounds of the invention and the length of the treatment period will vary with the nature and severity of the condition to be treated, with the mammal involved, with the organ transplanted, and with the particular compound of the invention and its route of administration.

The compounds of the invention may be assayed for the treatment of transplant-related arteriosclerosis using methods known in the art; e.g., Haber et al., U.S. Pat. No. 5,675,062, Oct. 7, 1997.

For compounds of formula I, the daily dose range lies in the range of 200 to 0.001 mg/kg body weight of a mammal, preferably 100 to 1 mg/kg, and most preferably 90 to 10 mg/kg, in single or divided doses. In some cases, it may be necessary to use doses outside these ranges. When a composition for intravenous administration is employed, a suitable daily dosage range is from about 60 to 0.05 mg (preferably 50 to 0.01 mg) compound of the invention per kg body weight. When a composition for oral administration is employed, a suitable daily dosage range is from about 20 to 0.001 mg (preferably 10 to 0.01 mg) compound of the invention per kg body weight. When a composition for ophthalmic administration is employed, a suitable daily dosage range is from about 10–0.01% (preferably 5.0–0.5% compound of the invention, typically prepared as a 2.0–0.1% by weight solution or suspension of the compound in an acceptable ophthalmic formulation.

For compounds of formula II, the daily dose range lies in the range of 10 to 0.05 mg/kg body weight of a mammal, preferably 7.5 to 0.5 mg/kg, and most preferably 5 to 1 mg/kg, in single or divided doses. In some cases, it may be necessary to use doses outside these ranges. When a composition for intravenous administration is employed, a suitable daily dosage range is from about 5 to 0.01 mg (preferably 1 to 0.05 mg) compound of the invention per kg body weight. When a composition for oral administration is employed, a suitable daily dosage range is from about 500 to 2.5 mg (preferably 250 to 5 mg) compound of the invention per kg body weight.

Any suitable route of administration may be employed for providing a mammal, especially a human, with an effective dosage of the compounds of the invention. For example, oral, rectal, topical, parenteral, ocular, pulmonary, nasal, etc. routes may be employed. Dosage forms include tablets, troches, dispersions, suspensions, solutions, capsules, creams, ointments, aerosols, and the like. The routes of administration may be the same or different for each of the two compounds.

The pharmaceutical compositions of the present invention comprise the compounds of formula I and formula II, either in intimate admixture or isolated from each other, or pharmaceutically acceptable salts thereof, as active ingredients, and may also contain pharmaceutically acceptable carriers and, optionally, other therapeutically active ingredients. The invention includes such compositions for use in the treatment of transplant-associated arteriosclerosis.

The dosage forms described herein may contain one or both of the compounds of formula I and II.

The compositions include compositions suitable for oral, rectal, topical (including transdermal devices, aerosols, creams, ointments, lotions, and dusting powders), parenteral (including subcutaneous, intramuscular, and intravenous), ocular (ophthalmic), pulmonary (nasal or buccal inhalation), or nasal administration; although the most suitable route in any given case will depend largely on the nature and severity of the condition being treated and on the nature of the active ingredient. They may be conveniently presented in unit dosage form and prepared by any of the methods well known in the art of pharmacy.

For example, compounds of the invention may be administered orally, for example in tablet form, or by inhalation, for example in aerosol or other atomisable formulations or in dry powder formulations, using an appropriate inhalation device such as those known in the art. The compounds of the invention may also be administered intranasally.

A compound of the invention may be combined as the active ingredient in intimate admixture with a pharmaceutical carrier according to conventional pharmaceutical compounding techniques. The carrier may take a wide variety of forms depending on the nature of the preparation desired for administration, i.e., oral, parenteral, etc. In preparing oral dosage forms, any of the usual pharmaceutical media may be used, such as water, glycols, oils, alcohols, flavoring agents, preservatives, coloring agents, and the like in the case of oral liquid preparations (e.g., suspensions, elixirs, and solutions); or carriers such as starches, sugars, microcrystalline cellulose, diluents, granulating agents, lubricants, binders, disintegrating agents, etc. in the case of oral solid preparations such as powders, capsules, and tablets. Solid oral preparations are preferred over liquid oral preparations. Because of their ease of administration, tablets and capsules are the preferred oral dosage unit form. If desired, capsules may be coated by standard aqueous or non-aqueous techniques.

In addition to the dosage forms described above, the compounds of the invention may be administered by controlled release means and devices.

Pharmaceutical compositions of the present invention suitable for oral administration may be prepared as discrete units such as capsules, cachets, or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general, the compositions are prepared by uniformly and intimately admixing the active ingredient with liquid carriers, finely divided solid carriers, or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as powder or granule optionally mixed with a binder, lubricant, inert diluent, or surface active or dispersing agent. Molded tablets may be made by molding in a suitable machine, a mixture of the powdered compound moistened with an inert liquid diluent.

Ophthalmic inserts are made from compression molded films which are prepared on a Carver Press by subjecting the powdered mixture of active ingredient and HPC to a compression force of 12,000 lb. (gauge) at 149° C. for 1–4 min. The film is cooled under pressure by having cold water circulate in the platen. The inserts are then individually cut from the film with a rod-shaped punch. Each insert is placed in a vial, which is then placed in a humidity cabinet (88% relative humidity at 30° C.) for 2–4 days. After removal from the cabinet, the vials are capped and then autoclaved at 121° C. for 0.5 hr.

The inhalable form may be, for example, an atomisable composition such as an aerosol comprising the compounds of the invention in solution or dispersion in a propellant or a nebulizable composition comprising a dispersion of the compound of the invention in an aqueous, organic or aqueous/organic medium, or a finely divided particulate form comprising the compounds of the invention in finely divided form optionally together with a pharmaceutically acceptable carrier in finely divided form.

The compositions containing a compound of this invention may also comprise an additional agent selected from the group consisting of cortiocosteroids, bronchodilators, anti-asthmatics (mast cell stabilizers), anti-inflammatories, antirheumatics, immunosuppressants, antimetabolites, immunomodulators, antpsoriatics, and antidiabetics. Specific compounds include theophylline, sulfasalazine and aminosalicylates (anti-inflammatories); cyclosporin, FK-506, and rapamycin (immunosuppressants); cyclophosphamide and methotrexate (antimetabolites); and interferons (immunomodulators).

An aerosol composition suitable for use as the inhalable form may comprise the compound of the invention in solution or dispersion in a propellant, which may be chosen from any of the propellants known in the art. Suitable such propellants include hydrocarbons such as n-propane, n-butane or isobutane or mixtures of two or more such hydrocarbons, and halogen-substituted hydrocarbons, for example fluorine-substituted methanes, ethanes, propanes, butanes, cyclopropanes or cyclobutanes, particularly 1,1,1,2-tetrafluoroethane (HFA134a) and heptafluoropropane (HFA227), or mixtures of two or more such halogen-substituted hydrocarbons. Where the compounds of the invention are present in dispersion in the propellant, i.e. where present in particulate form dispersed in the propellant, the aerosol composition may also contain a lubricant and a surfactant, which may be chosen from those lubricants and surfactants known in the art. The aerosol composition may contain up to about 5% by weight, for example 0.002 to 5%, 0.01 to 3%, 0.015 to 2%, 0.1 to 2%, 0.5 to 2% or 0.5 to 1%, by weight of the compounds of the invention, based on the weight of the propellant. Where present, the lubricant and surfactant may be in an amount up to 5% and 0.5% respectively by weight of the aerosol composition. The aerosol composition may also contain ethanol as co-solvent in an amount up to 30% by weight of the composition, particularly for administration from a pressurized metered dose inhalation device.

A finely divided particulate form, i.e. a dry powder, suitable for use as the inhalable form may comprise the compounds of the invention in finely divided particulate form, optionally together with a finely divided particulate carrier, which may be chosen from materials known as carriers in dry powder inhalation compositions, for example saccharides, including monosaccharides, disaccharides and polysaccharides such as arabinose, glucose, fructose, ribose, mannose, sucrose, lactose, maltose, starches or dextran. As especially preferred carrier is lactose. The dry powder may be in capsules of gelatin or plastic, or in blisters, for use in a dry powder inhalation device, preferably in dosage units of 5 µg to 40 mg of the active ingredient. Alternatively, the dry powder may be contained as a reservoir in a multi-dose dry powder inhalation device.

In the finely divided particulate form, and in the aerosol composition where the compounds of the invention are present in particulate form, the compound of the invention may have an average particle diameter of up to about 10 µm, for example 1 to 5 µm. The particle size of the compound of the invention, and that of a solid carrier where present in dry powder compositions, can be reduced to the desired level by conventional methods, for example by grinding in an air-jet mill, ball mill or vibrator mill, microprecipitation, spray-drying, lyophilisation or recrystallisation from supercritical media.

The inhalable medicament may be administered using an inhalation device suitable for the inhalable form, such devices being well known in the art. Accordingly, the invention also provides a pharmaceutical product comprising the compounds of the invention in inhalable form as hereinbefore described in association with an inhalation device. In a further aspect, the invention provides an inhalation device containing the compounds of the invention in inhalable form as hereinbefore described.

Where the inhalable form is an aerosol composition, the inhalation device may be an aerosol vial provided with a valve adapted to deliver a metered dose, such as 10 to 100 µl, e.g. 25 to 50 µl, of the composition, i.e. a device known as a metered dose inhaler. Suitable such aerosol vials and procedures for containing within them aerosol compositions under pressure are well known to those skilled in the art of inhalation therapy. Where the inhalable form is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 mL, commonly 1 to 10 mL, of the dispersion; or a hand-held nebulizer such as an AERX (ex Aradigm, US) or BINEB (Boehringer Ingelheim) nebulizer which allows much smaller nebulized volumes, e.g. 10 to 100 µl, than conventional nebulizers. Where the inhalable form is the finely divided particulate form, the inhalation device may be, for example, a dry powder inhalation device adapted to deliver dry powder from a capsule or blister containing a dosage unit of the dry powder or a multidose dry powder inhalation device adapted to deliver, for example, 25 mg of dry powder per actuation. Suitable such dry powder inhalation devices are well known.

The compounds of formula I may be synthesized using known techniques. See, e.g., WO 96/22966, incorporated herein by reference, which teaches the synthesis of analogous compounds. For compounds α-η, undefined symbols are as defined for compounds of formula I. For example, representative compounds of formula I wherein W is CH are prepared by reacting a compound of formula α

$$R_1-(CH_2)_p-Y-OH \qquad (\alpha)$$

wherein $R_1$, p, and Y are as defined above, or a reactive functional derivative thereof, With a compound of the formula β

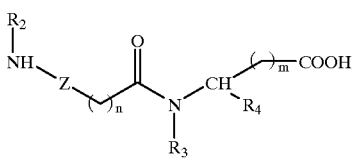

(β)

wherein the carboxyl group is in protected form and wherein $R_2$—$R_4$, Z, n, and m are as defined above, and if desired, converting a compound so obtained to another compound of the invention. The condensation is carried out according to methodology well known in the art for amide formation, e.g. in the presence of a condensing agent such as 1-[3-(dimethylamino)propyl]-3-ethylcarbodiimide hydrochloride and a base, such as diisopropylethylamine, in an inert solvent (such as methylene chloride), preferably at room temperature.

The starting materials of formula α, such as optionally substituted phenyl-ureidophenylacetic acids, are in turn known in the art or are prepared according to methods known in the art, e.g. by, for example, condensing a p-aminophenylacetic acid ester with the appropriate aryl isocyanate to obtain the corresponding phenylureido-phenylacetic acid ester and hydrolyzing the resulting ester.

The starting materials of formula p are in turn prepared by reacting a compound of the formula γ

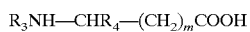  (γ)

wherein the carboxyl group is in protected form (e.g., as an alkyl ester) and $R_3$, $R_4$, and m are as defined above, with a compound of the formula δ

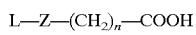  (δ)

preferably as a reactive functional derivative thereof, wherein Z is $(CH_2)_n$, or $CHR_6$, and n, n' and $R_6$ are as defined above and L is a leaving group, such as halo or (alkyl or aryl)-sulfonyloxy, in the presence of a base, such as triethylamine, to obtain a compound of the formula ε

(ε)

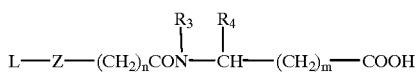

wherein the carboxylic acid is in protected form (e.g. as an alkyl ester), and L, $R_1$, $R_2$, and Z are as defined above, which is in turn reacted with an amine of the formula η

  (η)

wherein $R_2$ is as defined above under conditions well-known in the art, to obtain a starting material of formula β in protected form (e.g., as an alkyl ester). Hydrolysis, e.g. with base, such as aqueous lithium hydroxide, gives a starting material of formula β.

The cited processes may be carried out while, if necessary, temporarily protecting any interfering reactive group(s), and then liberating the resulting compound of the invention. In starting compounds and intermediates which are converted to the compounds of the invention in a manner described herein, functional groups present, such as carboxyl, amino and hydroxy groups, are optionally protected by conventional protecting groups that are a common in preparative organic chemistry. Well-known protecting groups and their introduction are described, for example, in J. F. W. McOmie, "Protective Groups in Organic Chemistry", Plenum Press, London, N.Y., T. W. Greene, "Protective Groups in Organic Synthesis", Wiley, N.Y. For example, a hydroxy group is advantageously protected in the form of a benzyl ether which can be cleaved by catalytic hydrogenation to obtain a hydroxy substituted product.

The resulting compounds of formula I wherein X is esterified carboxyl ($COOR_5$) can be converted to the corresponding acids e.g. by hydrolysis according to methods well-known in the art.

The abbreviations used in the following Examples have the indicated meaning:

| | |
|---|---|
| conc. = | concentrated |
| DEIA = | di-isopropylethylamine |
| DMSO = | dimethyl sulfoxide |
| EDAC = | 1-[3-(dimethylamino)propyl]-3-ethylcarbodiimide hydrochloride |
| HOBT = | hydroxybenzotriazole |
| HOSu = | hydroxysuccinamide |
| HPLC = | high pressure liquid chromatography |
| MS = | mass spectroscopy |
| NMR = | nuclear magnetic resonance |
| OR = | optical rotation |
| TEA = | triethylamine |
| TLC = | thin layer chromatography |
| TRIS = | tris(hydroxymethyl)aminomethane |

The invention is further defined by the examples, which are intended to be illustrative and not limiting. Temperatures are in degrees Celsius.

COMPOUNDS OF FORMULA I

EXAMPLE 1

(S)-β-[3-Methoxypropyl)[[4-[(2-methylphenylaminocarbonyl-amino)phenyl]acetyl]amino]acetylamino-benzenepropanoic Acid Step 1

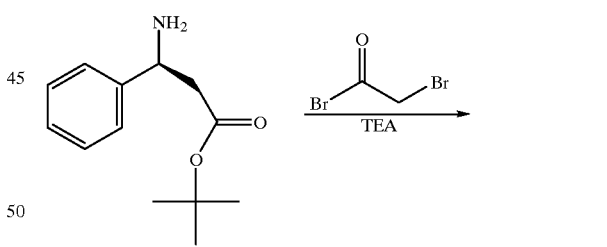

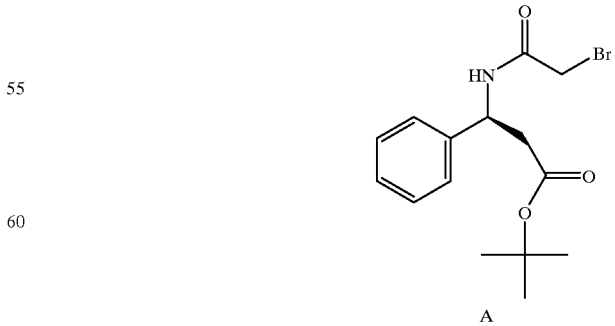

A

To 45 mL $CH_2Cl_2$ 1 g (4.5 mmol) 1,1-dimethyl ethyl (3S)-3-amino-3-phenylpropanoate is added. Then 0.720 mL (5.17 mmol) TEA is added. The mixture is stirred 10 min., and cooled 0° C. To the mixture is added 0.450 mL (5.17 mmol) bromoacetyl bromide in 5 mL CH$_2$Cl$_2$ dropwise over 15 min. The mixture is stirred over 3 hrs., allowing it to reach room temp. TLC, using 50% ethyl acetate/50% hexanes, is used to monitor the reaction. The mixture is reduced to dryness and flash chromatographed using 30 g silica gel, Merck, grade 9385, 230–400 mesh, 60 A, using 25% ethyl acetate /75% hexanes, to yield 1.75 g thick yellow oil, which shows one spot on TLC. The product is carried on to the next step.

Step 2

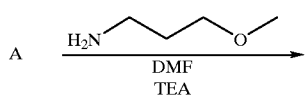

A

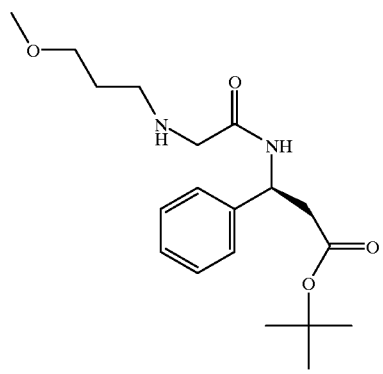

B

To 50 mL DMF is added 1.5 g A and 1.0 g (11 mmol) 3-methoxy- propylamine. At room temp. 0.74 mL (5.3 mmol) triethylamine is added. The mixture is stirred 16 hrs. at room. temp. TLC, using 10% CH$_3$OH/90% CH$_2$Cl$_2$, is used to monitor the reaction. The mixture is reduced to dryness and flash chromatographed using 45 g silica gel, starting with 2% and gradually increasing to 4% CH$_3$OH/CH$_2$Cl$_2$, to yield 1.6 g yellow oil, which shows one spot on TLC. The product is carried on to the next step.

Step 3

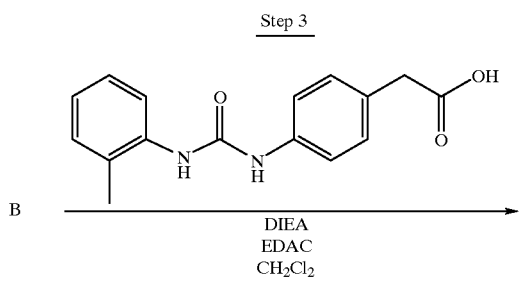

B $\xrightarrow{\text{DIEA, EDAC, CH}_2\text{Cl}_2}$

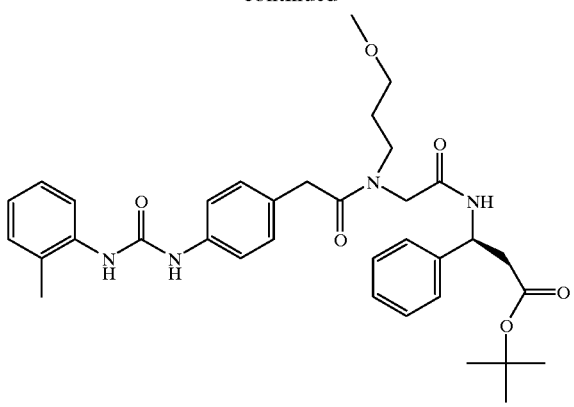

C

To 50 mL CH$_2$Cl$_2$ is added 1.5 g B. Then 1.4 g (4.8 mmol) N-(2-methyl)-N'-(4'-acetic acid) diphenyl urea (only partially soluble) and 0.74 mL (5.3 mmol) DIEA is added. The mixture is stirred 15 min. at room temp. to give a clear yellow solution. 0.98 g (4.8 mmol) EDAC is added and the mixture stirred 3 hrs. TLC, using 10% CH$_3$OH/90% CH$_2$Cl$_2$, is used to monitor the reaction. The mixture is reduced to dryness and flash chromatographed using 90 g silica gel, starting with 1% and increasing to 5% CH$_3$OH/CH$_2$Cl$_2$, to yield 1.93 g white foam.

Step 4

C $\xrightarrow{20\% \text{ TFA/CH}_2\text{Cl}_2}$

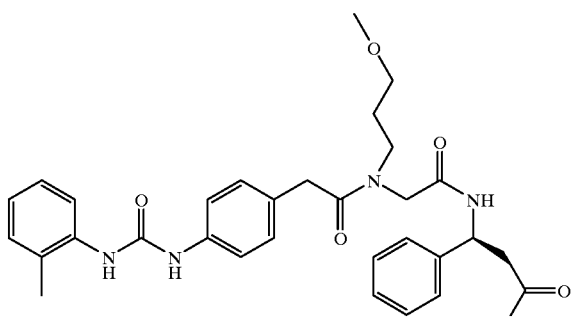

To 35 mL CH$_2$Cl$_2$ at room temp is added 1.7 g C. Then 8 mL TFA acid is added dropwise with 5 mL CH$_2$Cl$_2$. The mixture is stirred 2 hrs. TLC, using 10% CH$_3$OH/90% CH$_2$Cl$_2$, is used to monitor the reaction. The mixture is reduced to dryness. Fresh CH$_2$Cl$_2$ is added several times to remove all TFA. The product is flash chromatographed using 50 g silica gel and 2% to 5% CH$_3$OH/CH$_2$Cl$_2$ to yield 1.5 g of the title compound as a white powder.

mp: 125–1270° C.; OR: −27.4°, DMSO (10 mg/mL).

EXAMPLE 2

(S)-[3-Methoxypropyl)[[4-[(2-methylphenylaminocarbonylamino)-phenyl]acetyl]amino]acetylamino-4-hexanoic Acid Step 1

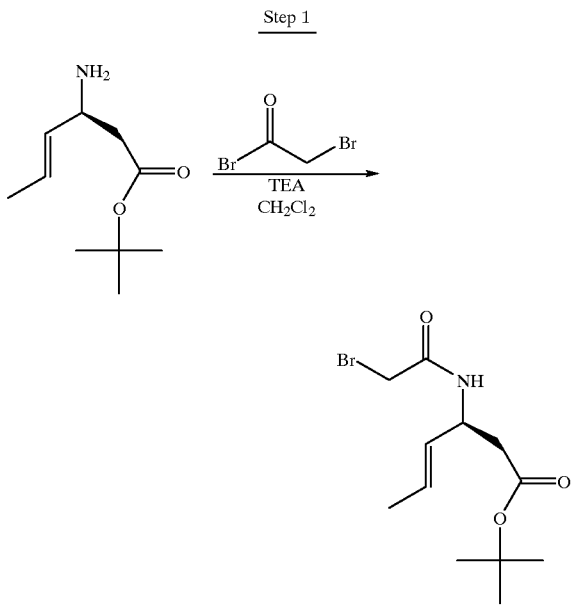

Following the procedure of Example 1, step 1, but starting with 0.834 g (4.5 mmol) 1,1-dimethyl ethyl(3S)-3-amino-4-hexeneoate there is obtained 01.46 g thick yellow oil, which shows one spot on TLC. The product is carried on to the next step.

Step 2

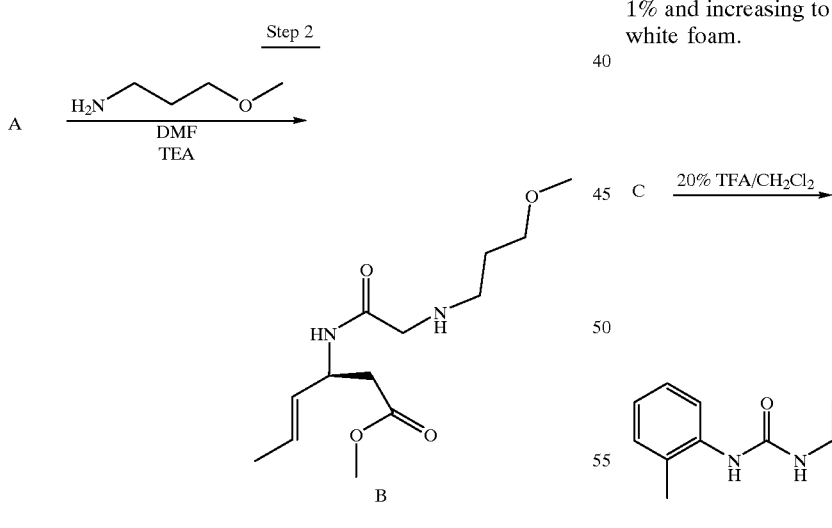

To 10 mL DMF is added 0.31 g (1 mmol) A. Then 0.18 g (2 mmol) 3-methoxy-propylamine is added. At room temp. 0.23 mL (2 mmol) TEA is added. The mixture is stirred 16 hrs. at room. temp. TLC, using 10% $CH_3OH$/90% $CH_2Cl_2$, is used to monitor the reaction. The mixture is reduced to dryness and flash chromatographed using 12 g silica gel, starting with 2% and gradually increasing to 4% $CH_3OH$/$CH_2Cl_2$, to yield 0.1 g yellow oil, which shows one spot on TLC. The product is carried on to the next step.

Step 3

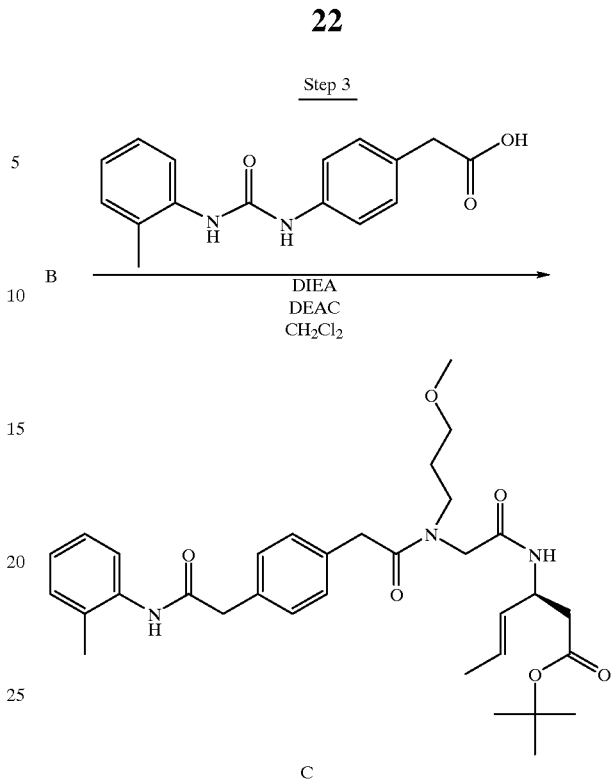

To 50 mL $CH_2Cl_2$ is added 1.4 g (4.4 mmol) B. Then 1.4 g (4.8 mmol) N-(2-methyl)-N'-(4'-acetic acid) diphenyl urea, only partially soluble, and 0.74 mL (5.3 mmol) DIEA are added and the mixture stirred 15 min. to give a clear yellow solution. 0.98 g (4.8 mmol) EDAC is added and the mixture stirred 3 hrs. TLC, using 10% $CH_3OH$ in $CH_2Cl_2$, is used to monitor the reaction. The mixture is reduced to dryness, flashed chromatographed using 90 g silica gel, starting with 1% and increasing to 5% $CH_3OH$ in $CH_2Cl_2$, to yield 1.8 g white foam.

Step 4

To 35 mL $CH_2Cl_2$ at room temp is added 1.7 g C. Then 8 mL TFA is added dropwise with 5 mL $CH_2Cl_2$. The mixture is stirred 2 hrs. TLC, using 10% $CH_3OH$/90% $CH_2CL_2$, is used to monitor the reaction. The mixture is reduced to dryness. Fresh $CH_2Cl_2$ is added several times to remove all TFA. The product is flash chromatographed using 50 g silica gel and 2% to 5% $CH_3OH$/$CH_2Cl_2$ to yield 1.5 g of the title compound as a white powder.

mp: 88–90° C.;

EXAMPLE 3

(S)-β-[3-Methoxypropyl)[[4-[(2-methylphenylaminocarbonylamino)-phenyl]acetyl]amino]acetylamino-3,4-dimethoxy-benzenepropanoic Acid Step 1

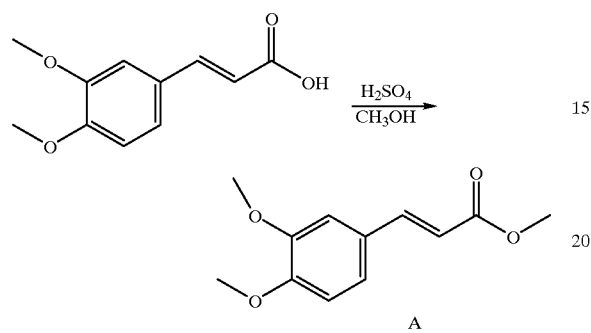

A

To 300 mL CH₃OH is 30 g (144.2 mmol) 3,4-dimethoxycinnamic acid. Four drops H₂SO₄ is added and the mixture refluxed for 4 hrs. TLC, using 70/30 ethyl acetate/ hexanes, is used to monitor the reaction. The mixture is reduced to dryness and flash chromatographed, using 20% ethyl acetate/80% hexanes, on 350 g silica gel, grade 60, 70–230 mesh, to yield 14.14 g A.

Step 2

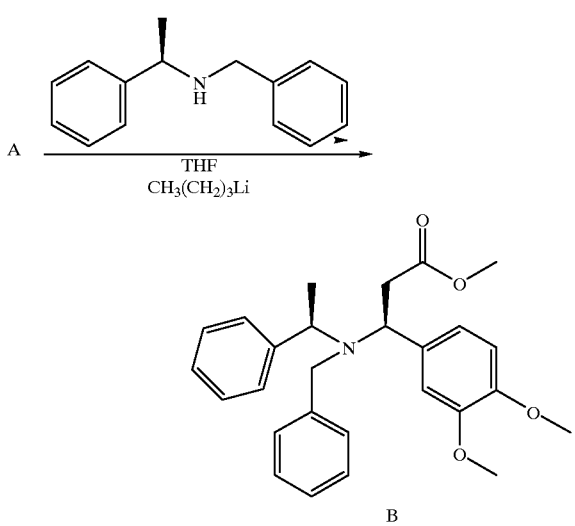

B

To 200 mL THF is added 11.8 g (55.8 mmol) (R)-(+)-N-benzyl α-methylbenzylamine. The mixture is cooled to 0° C. and 34.9 mL (55.8 mmol) n-buLi (1.6 M in hexanes) added dropwise over 30 min. The mixture is stirred for an 30 additional min. The reaction is cooled to −78° C. Then 6.2 g (27.9 mmol) methyl 3,4-dimethoxycinnamate, dissolved in 150 mL THF, is added dropwise over 1 hr. The mixture is stirred for 30 min. at −78° C. and slowly, maintaining −78° C., 25 mL saturated NH₄Cl solution is added and the mixture warmed to room temp., ished with brine, and reduced to dryness. TLC, using 50/50 ethyl acetate/hexanes, is used to monitor the reaction. The mixture is flashed chromatographed on 180 g silica gel, Merck, grade 9385, 230–400 mesh, 60A, to yield 10.5 g thick yellow oil.

Step 3

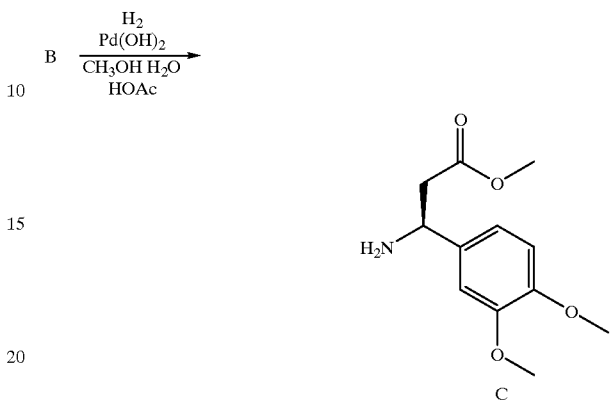

C 5.0 g (11.5 mmol) B is added to 250 mL CH₃OH, 25 mL H₂O, and 7.5 mL HOAc. 1 g Pearlman's catalyst (Pd (OH)₂) is added. Using a ballon, the mixture is refluxed in an H₂ atmosphere for 16 hrs. at room temp. TLC, using 5% CH₃OH/CH₂Cl₂, is used to monitor the reaction. The mixture is filtered through celite, washed with CH₃OH, and reduced to dryness. To the dry product is added CH₂Cl₂ and it is ished with brine made basic with sat'd NaHCO₃. The mixture is reduced to dryness and flash chromatographed using 150 g silica gel, 230–400 mesh, 1 to 4% CH₃OH/CH₂Cl₂, to yield 1.54 g yellow oil.

Step 4

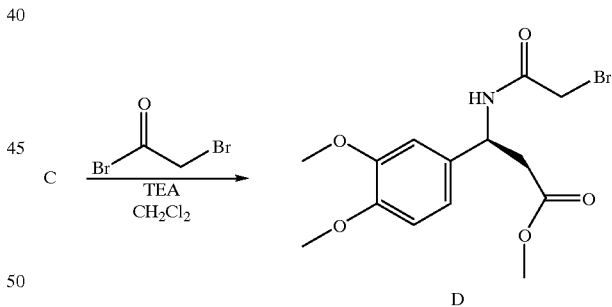

D

To 9 mL CH₂Cl₂ is added 0.2 g (0.8 mmol) C and 0.13 mL (0.9 mmol) TEA. The mixture is stirred 10 min. and the mixture cooled to 0° C. 0.08 mL (0.9 mmol) bromoacetyl bromide in 1 mL CH₂Cl₂ is added dropwise over 15 min. The mixture is stirred over 3 hrs. allowing the mixture to reach room temp. TLC, using 50% ethyl acetate/50% hexanes, is used to monitor the reaction. The mixture is reduced to dryness and flash chromatographed using 30 g silica gel, Merck, grade 9385, 230–400 mesh, 60 A, using 25% ethyl acetate/75% hexanes, to yield 0.237 g thick yellow oil, which shows one spot on TLC. The product is carried on to the next step.

Step 5

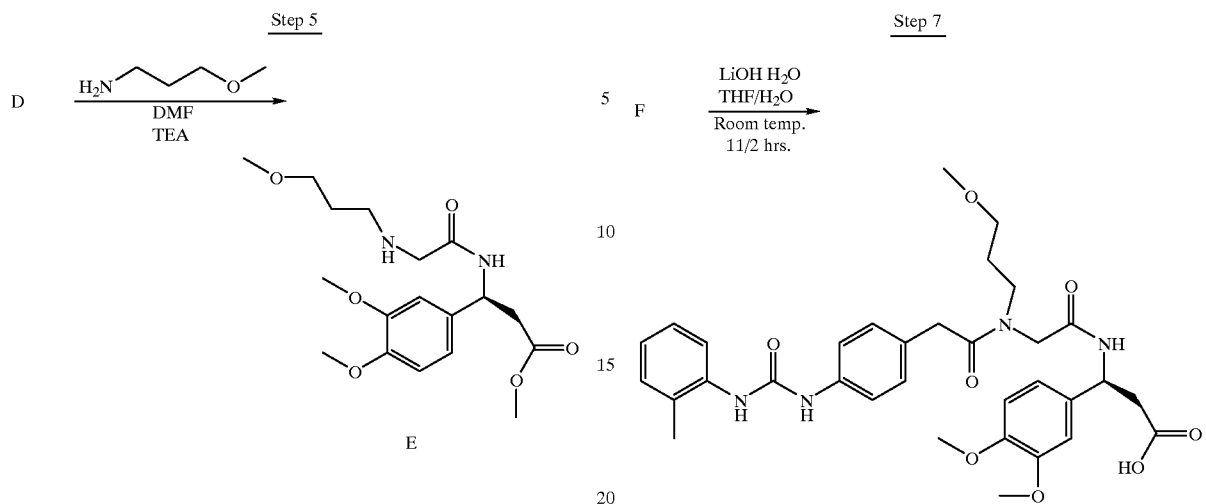

To 10 mL DMF are added 0.36 g (1 mmol) D and 0.18 g (2 mmol) 3-methoxypropylamine. At room temp. 0.23 mL TEA is added. The mixture is stirred 16 hrs. at room. temp. TLC, using 10% $CH_3OH$/90% $CH_2Cl_2$, is used to monitor the reaction. The mixture is reduced to dryness and flash chromatographed using 12 g silica gel, starting with 2% and gradually increasing to 4% $CH_3OH$/$CH_2Cl_2$, to yield 0.1 g yellow oil, which shows one spot on TLC. The product is carried on to the next step.

Step 6

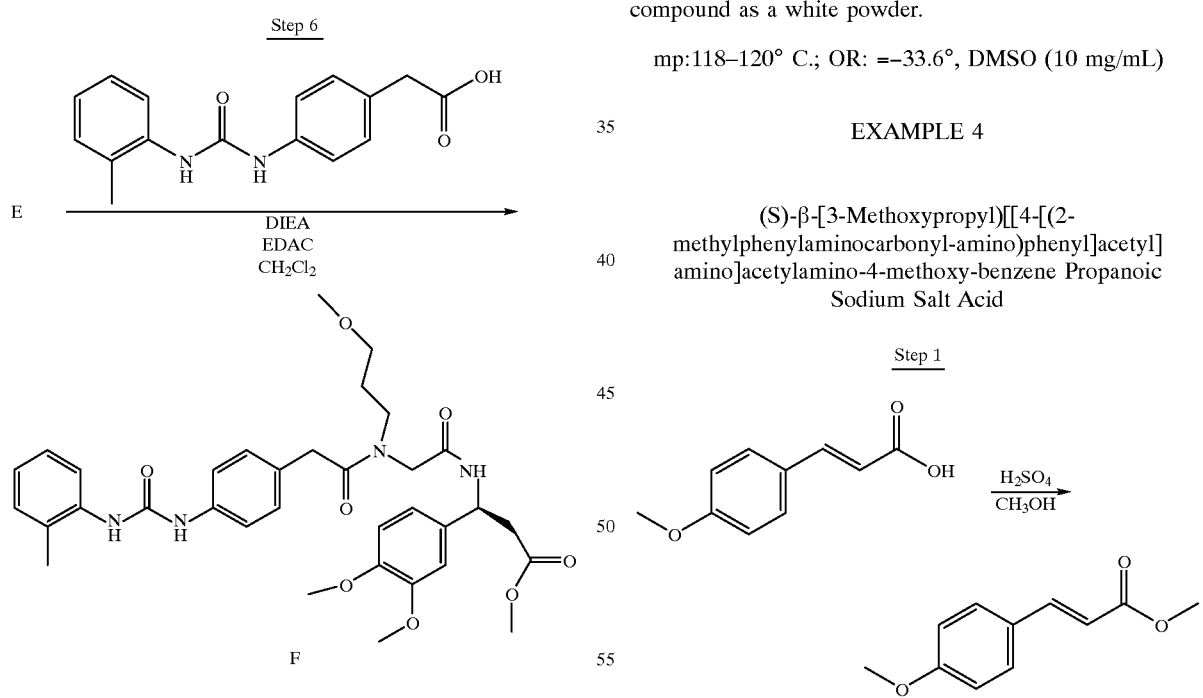

To 5 mL $CH_2Cl_2$ is added 0.1 g (0.27 mmol) E and 0.0853 g (0.30 mmol) N-(2-methyl)-N'-(4'-acetic acid) diphenyl urea, which is only partially soluble. 0.056 mL (0.34 mmol) DIEA is added and the mixture stirred 15 min. at room temp. to give a clear yellow solution. 0.058 g (0.30 mmol) EDAC is added and the mixture stirred 3 hrs. TLC, using 10% $CH_3OH$/90% $CH_2Cl_2$, is used to monitor the reaction. The mixture is reduced to dryness, flash chromatographed using 90 g silica gel, using 1% increasing to 5% $CH_3OH$/$CH_2Cl_2$, to yield 0.113 g white foam.

Step 7

To 21 mL THF and 8 mL $H_2O$ is added 0.36 g (0.57 mmol) F. 0.36 g (0.86 mmol) LiOH dissolved in 1 mL $H_2O$ is added dropwise over 5 min. and the mixture stirred for two hrs. at room temp. TLC, using 10% $CH_3OH$/$CH_2Cl_2$, is used to monitor the reaction. The mixture is reduced to dryness and flash chromatographed on 20 g silica gel, using 100% $CH_2Cl_2$ to 5% $CH_3OH$/$CH_2Cl_2$, to yield 0.36 g of the title compound as a white powder.

mp:118–120° C.; OR: =−33.6°, DMSO (10 mg/mL)

EXAMPLE 4

(S)-β-[3-Methoxypropyl)[[4-[(2-methylphenylaminocarbonyl-amino)phenyl]acetyl]amino]acetylamino-4-methoxy-benzene Propanoic Sodium Salt Acid

Step 1

To 250 mL $CH_3OH$ is added 50 g (280.8 mmol) 4-dimethoxycinnamic acid and 2 mL conc. $H_2SO_4$. The mixture is refluxed for 6 hrs. TLC, using 70/30 ethyl acetate/hexanes, is used to monitor the reaction. About 30 mL $CH_3OH$ is removed. The mixture is cooled to r.t, and then crystalized, filtered, ished with $H_2O$, and dried to yield 49.23 g of the desired product.

Step 2

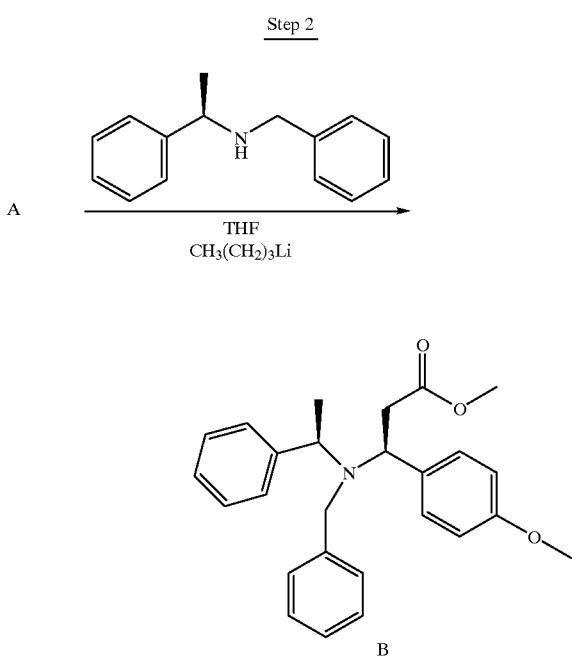

To 300 mL THF is added 10.99 g (52 mmol) (R)-(+)-N-benzyl-α-methylbenzylamine. The mixture is cooled to 0° C. and 32.5 mL (52 mmol) n-buLi (1.6 M in hexanes) added dropwise over 30 min. The mixture is stirred for an 30 additional min. The reaction is cooled to −78° C. Then 5 g (26 mmol) methyl 4-methoxycinnamate, dissolved in 100 mL THF, is added dropwise over 1 hr. The mixture is stirred for 30 min. at −78° C. and slowly, maintaining −78° C., 25 mL saturated NH$_4$Cl solution is added and the mixture warmed to room temp., washed with brine, and reduced to dryness. TLC, using 50/50 ethyl acetate/hexanes, is used to monitor the reaction. The mixture is flashed chromatographed on 180 g silica gel, Merck, grade 9385, 230–400 mesh, 60 Å to yield 9.738g thick pale-yellow oil (recrystalized from EtOAc/hexanes to give white crystals).

Step 3

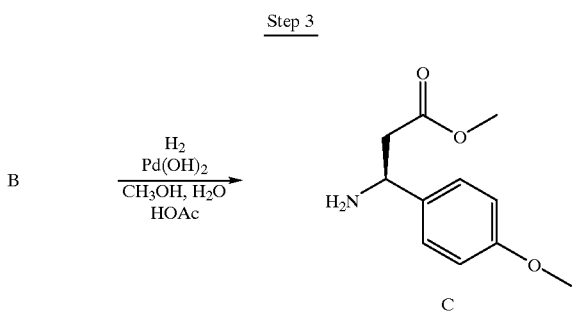

7.74 g (19.2 mmol) B is added to 250 mL CH$_3$OH, 25 mL H$_2$O, and 7.5 mL HOAc. 1 g Pearlman's catalyst is added. Using a hydrgen ballon, the mixture is refluxed in an H$_2$ atmosphere for 16 hrs. at room temp. TLC, using 5% CH$_3$OH/CH$_2$Cl$_2$, is used to monitor the reaction. The mixture is filtered through celite, washed with CH$_3$OH, and reduced to dryness. To the dry product added CH$_2$Cl$_2$ and it is washed with brine made basic with sat'd NaHCO$_3$. The mixture is reduced to dryness and flash chromatographed using 150 g silica gel, used 230–400 mesh, using 1 to 4% CH$_3$OH/CH$_2$Cl$_2$, to yield 3.4 g thick pale-yellow oil (recrystalized from EtOAc/hexanes to give white crystals).

Step 4

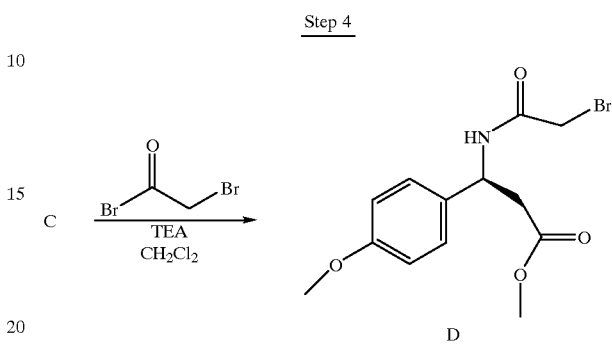

To 25 mL CH$_2$Cl$_2$. is added 0.8 g (3.82 mmol) C and 0.62 mL (4.4 mmol) TEA. The mixture is stirred 10 min. and the mixture cooled to 0° C. 0.38 mL (4.4 mmol) bromoacetyl bromide in 5 mL CH$_2$Cl$_2$ is added dropwise over 15 min. The mixture is stirred over 3 hrs. allowing the mixture to reach room temp. TLC, using 50% ethyl acetate/50% hexanes, is used to monitor the reaction. The mixture is reduced to dryness and flash chromatographed using 30 g silica gel, Merck, grade 9385, 230–400 mesh, 60 Å, using 25% ethyl acetate/75% hexanes, to yield 0.1.3 g thick yellow oil, which shows one spot on TLC. The product is carried on to the next step.

Step 5

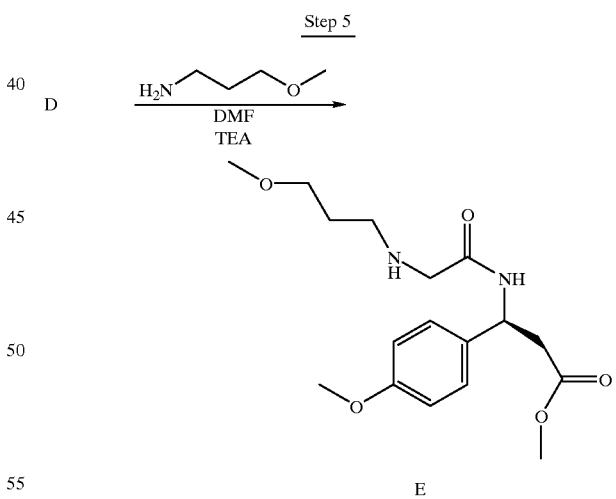

To 70 mL DMF are added 1.3 g (3.94 mmol) D and 0.667 g (7.49 mmol) 3-methoxypropylamine. At room temp. 0.1.05 mL (7.49 mmol) TEA is added. The mixture is stirred 16 hrs. at room. temp. TLC, using 10% CH$_3$OH/90% CH$_2$Cl$_2$, is used to monitor the reaction. The mixture is reduced to dryness and flash chromatographed using 75 g silica gel, starting with 2% and gradually increasing to 4% CH$_3$OH/CH$_2$Cl$_2$, to yield 1.29 g yellow oil which shows one spot on TLC. The product is carried on to the next step.

Step 6

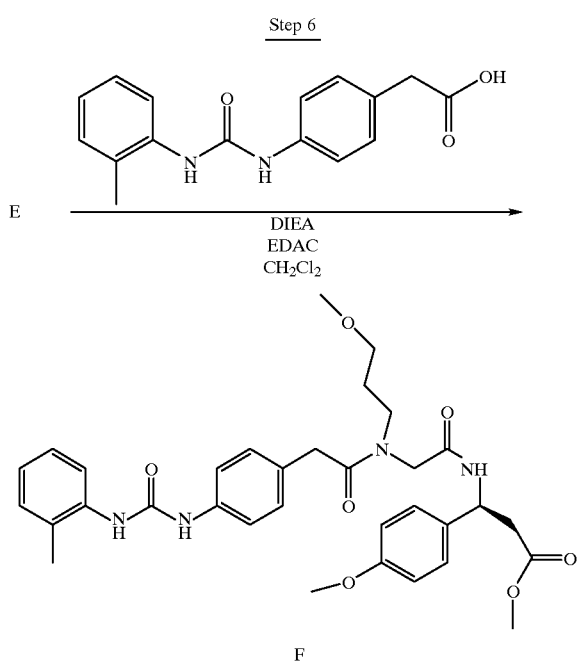

To 30 mL CH₂Cl₂ are added 0.72 g (2.1 mmol) E and 0.739 g (2.6 mmol) N-(2-methyl)-N'-(4'-acetic acid) diphenyl urea, which is only partially soluble. 0.46 mL (2.6 mmol) DIEA is added and the mixture stirred 15 min. at room temp. to give a clear yellow solution. 0.499 g (2.6 mmol) EDAC is added and the mixture stirred 3 hrs. TLC, using 10% $CH_3OH$/90% $CH_2Cl_2$, is used to monitor the reaction. The mixture is reduced to dryness, flash chromatographed using 90 g silica gel, using 1% increasing to 5% $CH_3OH/CH_2Cl_2$, to yield 0.920 g white foam.

Step 7

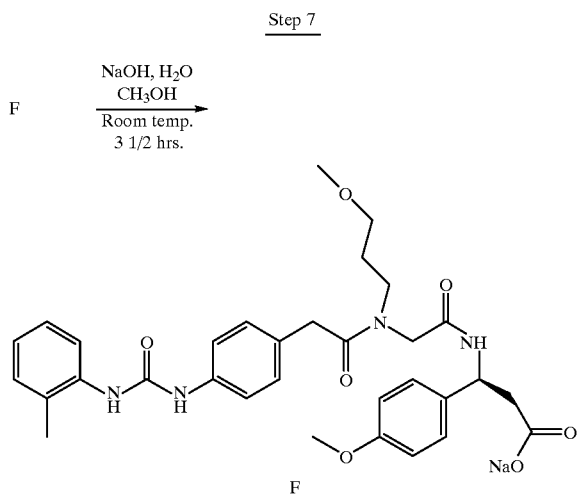

To 30 mL EtOH and 8 mL H₂O is added 0.90 g (1.49 mmol) F. To the mixture is added 0.057 g (1.42 mmol) NaOH in 1 mL H₂O. The mixture is stirred 3.5 hrs. at r.t. The mixture is filtered and dried to yield 0.720 g of the title compound as a white solid.

mp: 216–118° C. (dec); OR: −21.069° in DMSO (5.3 mg/mL).

EXAMPLE 5

Prepared similarly to the previous examples are the compounds of the formula

| Cmpd. | $R_a$ | T | $R_2$ | $R_4$ | m.p.(° C.) |
|---|---|---|---|---|---|
| (a) | $CH_3$ | NH | $(CH_2)_4OCH_3$ | 3,4-dimethoxyphenyl | 114–117 (dec) |
| (b) | $CH_3$ | NH | $(CH_2)_4OCH_3$ | Phenyl | 116–118 (dec) |
| (c) | $CH_3$ | $CH_2$ | $(CH_2)_3OCH_3$ | 4-methoxyphenyl | 127–130 (dec) |
| (d) | H | NH | $(CH_2)_3OCH_3$ | Phenyl | 107–111 (dec) |
| (e) | Cl | NH | $(CH_2)_3OCH_3$ | Phenyl | 118–122 |
| (f) | $NH_2$ | NH | $(CH_2)_3OCH_3$ | Phenyl | 105–109 (dec) |

COMPOUNDS OF FORMULA II

The compounds of formula II are prepared according to the processes of PCT application WO 96/03430.

TEST PROTOCOL

The effect of compound 369 (VLA-4 antagonist) and compound 741 (VCAM-1 inhibitor) on the development of transplant-associated arteriosclerosis as measured by neointimal formation in a mouse model of carotid artery transplantation is investigated as mono-, combined, and tolerance induction therapy. Grafts are harvested at 30 days post-transplantation. A synergistic effect is observed when compound 369+compound 741 are administered simultaneously following transplantation. Morphologically, neointimal formation is almost completely abolished, the medial layers are preserved, and no inflammatory cell infiltration in the adventitia is observed. This inhibitory effect is seen even when the two compounds are administered for the first 10 days only and the allografts are harvested at day 30 following transplantation.

Murine Carotid Artery Loop Transplantation

A murine model of accelerated transplant arteriosclerosis is used. Carotid arteries are allografted from B10.A (2R) to B10.BR mice, a commercially available strain combination that consistently results in neointimal formation 30 days after transplantation. The procedure is performed on anesthetized mice under a surgical dissecting microscope. A midline incision is made on the ventral side of neck from the suprasternal notch to the chin. The left carotid artery is gently dissected from the bifurcation in the distal end toward the proximal end as far as is technically possible. The artery is then occluded with two microvascular clamps, one at each end, and two longitudinal arteriotomies (0.5 to 0.6 mm) are made with a fine needle and scissors. In the donor mouse both the left and right carotid arteries are fully dissected from the arch to the bifurcation. The graft is then transplanted paratopically into the recipient in an end-to-side anastamosis with 11/0 continuous suture, and the skin incision is closed with a 5/0 interrupted suture. The ischemia time for each graft does not exceed 40 minutes. Vascular grafts are harvested 30 days after transplantation, a point at which a fully developed, nearly occlusive neointima is formed.

Dilution of Compound 369 and Compound 741

Compound 369 is dissolved in a mixture of dimethylsulfoxide (DMSO), 1 M Tris-phosphate buffer pH 8.8 and distilled water: the volume percentages are 2%, 15% and 83%, respectively. Compound 369 is initially dissolved in DMSO and heated to 37° C. Once the compound had fully dissolved, Tris buffer (37° C.) is added. If this solution is clear, the final volume of HPLC grade water is added.

Compound 741 is dissolved in a 1:1 mixture of CsA placebo solution (each mL contains 650 mg of Cremphor and 32.9% ethanol) and propylene glycol. Compound 741 is very soluble in this mixture and the final solution is clear.

Anti VLA-4 antibody is diluted in sterile saline.

Monotherapy

Compound 369: In the monotherapy experiments, compound 369 is administered three times per day subcutaneously (s.c.) for a total daily dose of 90 mg/kg/day.

Compound 741: Compound 741 is administered continuously via alzet pump in a dose of 5.0, 1.0, and 0.5 mg/kg/day, respectively.

Anti VLA-4 Mab: The anti VLA-4 antibody is administered 100 µg/mouse/d i.p.

Administration of a VLA-4 Mab at 100 µg/mouse/d i.p. fails to prevent the neointimal formation 30 days after transplantation in this model. Results for compound 369 and compound 741 are presented in Table 1.

Combination Therapy

A fixed dose of compound 369 is given as a total daily dose of 60 mg/kg/day s.c. and compound 741 is administered continuously via alzet pump at a dose of 5.0, 1.0, and 0.5 mg/kg/day, respectively.

Synergistic effects are observed when the compounds are administered in combination. Neointimal formation is almost completely abolished, the medial smooth muscle cell layer (SMCs) is well preserved, and inflammatory cell infiltration in the adventitia is suppressed. Histologically, the allografts resemble normal arteries.

Induction Therapy

Compound 369 (60 mg/kg/d) and compound 741 (5 mg/kg/d) are given simultaneously for the first 10 days only.

In all cases, allografts are harvested at day 30.

Compound 741 (5.0 mg/kg/d) and compound 369 (60 mg/kg, s.c.) are co-administered for the first 10 days only, during which time leukocytes would normally accumulate inside the lumen of the transplanted vessel. Allografts are harvested 30 days following transplantation. The histology is similar to that achieved with combined therapy. The results achieved with induction therapy are superior to those of monotherapy with either compound 741 or compound 369.

Histology

At the time of harvest, the animals are perfusion fixed with saline to remove residual blood followed by 4% paraformaldehyde for optimal fixation and preservation of tissue morphology. The transplanted loop is divided into two equal parts for subsequent processing. The proximal half of the loop (about 2.5 mm) is further fixed in 4% paraformaldehyde at 4° C. for 3 hours, processed and embedded in paraffin for morphometry analysis. The distal segment is immediately snap frozen in liquid nitrogen cooled isopentane following perfusion fixation and stored at −80° C. for future immunostaining purposes. The homogeneity of lesion formation in this model is confirmed, Shi et al., Proc. Natl. Acad. Sci., USA, 93, 4051–4056 (1996).

Histomorphometry

Morphometrical analysis is performed on VerHoeff stained paraffin sections using a computer-assisted image analysis system. The areas of the neointima are measured by computerized planimetry of sections obtained approximately 150, 300, and 450 µm from the center of the graft.

Data Analysis

Data from morphometric analyses are reported as the neointima area on cross-section determined by subtracting the new lumen area measurement from the internal elastic lamina (IEL) area measurement for each animal. Individual values (three per animal) are averaged and reported as the mean±SD.

The model is characterized by leukocyte infiltration inside the vessel lumen approximately 10 days after transplantation, followed by smooth muscle cell (SMC) migration and proliferation at day 15. A nearly occlusive neointima is formed by day 30 in which SMC and extracelluar matrix deposition predominate. As such, the NI area for the untreated group is 45,209±22,263 $\mu m^2$. Histologically, the medial layer is almost completely destroyed and leukocyte infiltration in both the media and adventitia is prominent 30 days after transplantation.

TABLE 1

Effect of Compounds 369 and 741 on neointimal formation

|  | Cmpd.741 5 mg/kg/d | Cmpd.741 1 mg/kg/d | Cmpd.741 0.5 mg/kg/d | Cmpd.741 0 mg/kg/d |
| --- | --- | --- | --- | --- |
| Cmpd.369 0 mg/kg/d | 18,804 ± 12,499 | 32,249 ± 15,943 | 30,926 ± 23,054 | 45,209 ± 22,263* |
| Cmpd.369 60 mg/kg/d | 1,556 ± 2,235 | 7,434 ± 8,669 | 50,384 ± 47,177 | 19,874 ± 14,348** |

*untreated group
**90 mg/kg/d compound 369

What is claimed is:

1. A pharmaceutical composition comprising synergistic effective amounts of a compound of formula Id

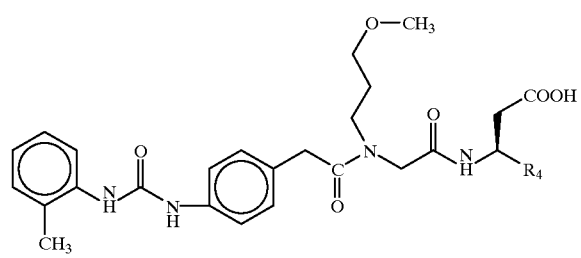

wherein $R_4$ is 3,4-dimethoxyphenyl;

and a compound of formula II'

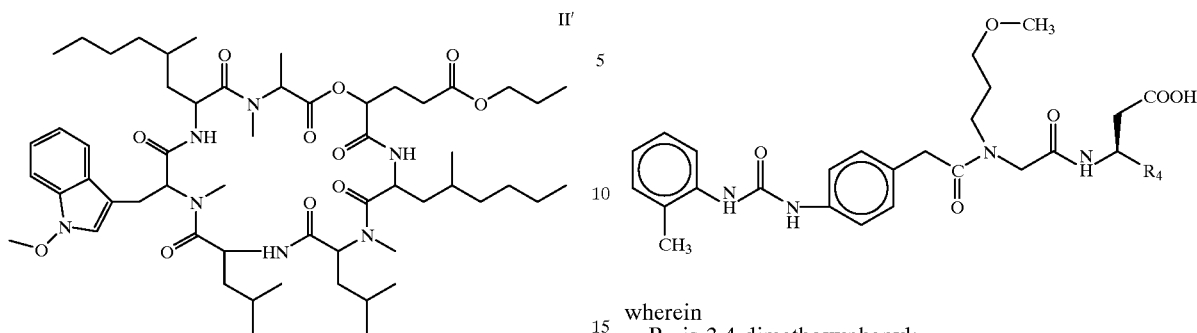

or the pharmaceutically acceptable salts thereof.

2. The concomitant administration to a mammal of a composition of claim 1 comprising 200 to 0.001 mg/kg body weight of a compound of formula Id and 10 to 0.05 mg/kg body weight of a compound of formula II' or pharmaceutically acceptable salts thereof.

3. The method of claim 2 wherein the mammal is man.

4. A method of treating transplant-associated arteriosclerosis in a mammal which comprises administering to a mammal in need of such treatment synergistic effective amounts of a compound of formula Id:

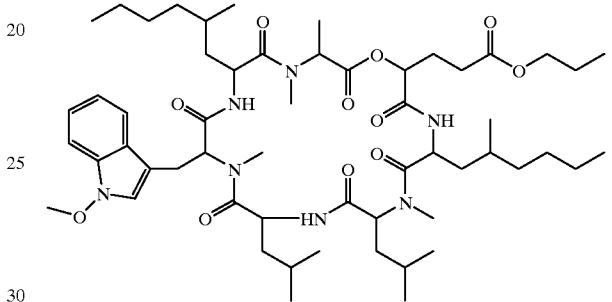

wherein
$R_4$ is 3,4-dimethoxyphenyl;
and of a compound of formula II'

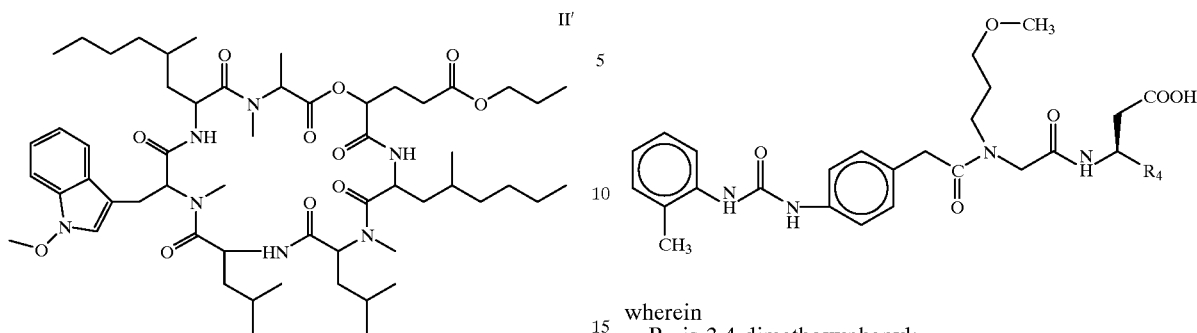

or pharmaceutically acceptable salts thereof; and, optionally, one or more pharmaceutically acceptable carriers.

5. A method of claim 4, wherein the mammal is man.

6. A method of claim 5, wherein the administration is intravenous.

7. A method of claim 5, wherein the administration is oral.

* * * * *